US006222544B1

(12) United States Patent
Tarr et al.

(10) Patent No.: US 6,222,544 B1
(45) Date of Patent: *Apr. 24, 2001

(54) GRAPHICAL USER INTERFACE FOR RADIATION THERAPY TREATMENT APPARATUS

(75) Inventors: Randall V. Tarr; Mark G. Wofford, both of Concord, CA (US)

(73) Assignee: Siemens Medical Systems, Inc., Iselin, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/953,780

(22) Filed: Oct. 17, 1997

(51) Int. Cl.[7] ................... G06F 3/14; A61N 5/01
(52) U.S. Cl. ............ 345/349; 345/348; 345/970; 345/961; 128/845; 600/427
(58) Field of Search ................ 128/920, 845; 378/65, 151, 150, 145, 158, 25; 600/427, 426, 407; 345/349, 965, 970, 961, 348, 339

(56) References Cited

U.S. PATENT DOCUMENTS

| 5,014,290 | * | 5/1991 | Moore et al. ............... 378/145 |
|---|---|---|---|
| 5,138,647 | | 8/1992 | Nguyen et al. ............. 378/189 |
| 5,148,032 | | 9/1992 | Hernandez ............... 250/492.1 |
| 5,247,555 | * | 9/1993 | Moore et al. ................. 378/4 |
| 5,347,627 | | 9/1994 | Hoffmann et al. ........... 395/157 |
| 5,394,452 | * | 2/1995 | Swerdloff et al. ............ 378/65 |
| 5,398,312 | | 3/1995 | Hoffmann ................. 395/156 |
| 5,438,991 | * | 8/1995 | Yu et al. ................. 600/426 |
| 5,563,925 | | 10/1996 | Hernandez ............... 378/150 |
| 5,594,859 | | 1/1997 | Palmer et al. ............. 395/330 |
| 5,661,773 | * | 8/1997 | Swerdloff et al. ........... 378/65 |
| 5,668,847 | | 9/1997 | Hernandez ................ 378/65 |
| 5,740,225 | * | 4/1998 | Nabatame ................. 378/65 |

OTHER PUBLICATIONS

European Patent Search Report dated Jun. 7, 1999.
Database Inspec ISBNO–89448–198–3 Institute of Electrical Engineers, Stevenage, GB Inspec No. Proceedings of the International Conference, 1995 DeMarco J. J; Soloberg T D; Wallace R E; Smathers JB; "Performance analysis of the Monte Carlo code MCNP4A for photonbased radiotherapy applications" XP002106317 *abstract*.
Database Inspec, ISSN0360–3016 Institute of Electrical Engineers, Stevenage, GB Inspec No. Int. J. Radiat.Oncol.Biol.Pys.(UK), UK,, May 15 1995 Chaney E L; Thorn J S; Tracton G; Cullip T; Rosenman J G; Tepper JE: "A portable reconstructed radiographs" XP0022106318 *abstract*.

* cited by examiner

Primary Examiner—Raymond J. Bayerl
Assistant Examiner—Thomas T. Nguyen

(57) ABSTRACT

A graphical user interface (1000) for use in a patient treatment system. The graphical user interface (1000) permits graphical display and editing of individual treatment parameters, including machine (2, 4, 6) positions and field shapes. Multiple fields grouped sequentially as an intensity modulated field (IMG) may be viewed as a superimposed graphical composite (1020, 1022, 1024, 1026). In addition, a pictorial representation of the radiation beams (1026) incident on a particular target is provided. A graphic representation of field shape (1030) is provided; the graphics change as treatment progresses. Finally, manipulation of graphics permits editing of treatment information, while allowing immediate feedback as to the result of the change.

26 Claims, 17 Drawing Sheets

FIG. 10

GRAPHICAL USER INTERFACE FOR RADIATION THERAPY TREATMENT APPARATUS

RESERVATION OF COPYRIGHT

A portion of the disclosure of this patent document contains material which is subject to copyright protection. The copyright owner has no objection to facsimile reproduction by anyone of the patent document or the patent disclosure as it appears in the Patent and Trademark Office patent file or records, as it becomes available to the public, but otherwise reserves all copyright rights whatsoever.

BACKGROUND OF THE INVENTION

1. Field of the Invention

The present invention relates to a radiation therapy system and, more particularly, to a system and method for efficiently delivering radiation treatment.

2. Description of the Related Art

Radiation emitting devices are generally known and used, for instance, as radiation therapy devices for the treatment of patients. A radiation therapy device generally includes a gantry which can be swiveled around a horizontal axis of rotation in the course of a therapeutic treatment. A linear accelerator is located in the gantry for generating a high energy radiation beam for therapy. This high energy radiation beam can be an electron beam or photon (X-ray) beam. During treatment, this radiation beam is trained on one zone of a patient lying in the isocenter of the gantry rotation.

To control the radiation emitted toward an object, a beam shielding device, such as a plate arrangement or a collimator, is typically provided in the trajectory of the radiation beam between the radiation source and the object. An example of a plate arrangement is a set of four plates that can be used to define an opening for the radiation beam. A collimator is a beam shielding device which could include multiple leaves, for example, a plurality of relatively thin plates or rods, typically arranged as opposing leaf pairs. The plates themselves are formed of a relatively dense and radiation impervious material and are generally independently positionable to delimit the radiation beam.

The beam shielding device defines a field on the object to which a prescribed amount of radiation is to be delivered. The usual treatment field shape results in a three-dimensional treatment volume which includes segments of normal tissue, thereby limiting the dose that can be given to the tumor. The dose delivered to the tumor can be increased if the amount of normal tissue being irradiated is decreased and the dose delivered to the normal tissue is decreased. Avoidance of delivery of radiation to the organs surrounding and overlying the tumor determines the dosage that can be delivered to the tumor.

The delivery of radiation by a radiation therapy device is prescribed and approved by an oncologist. The prescription is a definition of, for example, a particular volume and the level of radiation permitted to be delivered to that volume. Actual operation of the radiation equipment, however, is normally done by a therapist. When the therapist administers the actual delivery of the radiation treatment as prescribed by the oncologist, the radiation-emitting device is programmed to deliver that specific treatment. When programming the treatment, the therapist has to take into account the actual radiation output and has to adjust the dose delivery based on the plate arrangement opening to achieve the prescribed radiation treatment at the desired depth in the target.

The radiation therapist's challenge is to determine the best number of fields and delivered intensity levels to optimize the dose volume histograms, which define a cumulative level of radiation which is to be delivered to a specified volume. The outputs of the optimization engines are intensity maps, which are determined by varying the intensity at each "cell" in the map. The intensity maps specify a number of fields defining desired (optimized) intensity levels at each cell. The fields may be statically or dynamically modulated, such that a different accumulated dosage is received at different points in the field. Once radiation has been delivered according to the intensity map, the accumulated dosage at each cell, or dose volume histogram, should correspond to the prescription as closely as possible. In order to accurately deliver a treatment, a therapist may need to "edit" the radiation delivery from the output of the optimization engine.

In order to ensure accurate delivery of treatment, verify and record (V&R) methods are typically employed. The treatment is delivered only when all the parameters such as intensity levels, collimator leaf positions, and gantry angles have been met during the setup. As can readily be appreciated, patient treatment setup and verification information is nontrivial. Such information can include field size, gantry, collimator and table angles, dose and block and wedge codes. Typically, such information has been provided to the therapist by way of lengthy lists of numbers which must be translated into a useful form. Such lists are not only difficult to understand at a glance, but also are difficult to edit.

Accordingly, there is a need for an improved interface for display and editing of patient treatment information. There is a still further need for an improved method for monitoring and verifying ongoing treatment.

SUMMARY OF THE INVENTION

These problems in the prior art are overcome in large part by a system and method for radiation therapy delivery according to the present invention. A graphical user interface is provided for use in a patient treatment system. The graphical user interface permits graphical display and editing of individual treatment parameters, including machine positions and field shapes. Multiple fields grouped sequentially as an intensity modulated field may be viewed as a superimposed graphical composite. In addition, a pictorial representation of the radiation beams incident on a particular target is provided. A graphic representation of field shape is provided; the graphics change as treatment progresses. Finally, manipulation of graphics permits editing of treatment information, while allowing immediate feedback as to the result of the change.

BRIEF DESCRIPTION OF THE DRAWINGS

A better understanding of the present invention can be obtained when the following detailed description is considered in conjunction with the following drawings in which:

FIG. 10 is a diagram of other aspects of the graphical user interface of FIG. 5;

DETAILED DESCRIPTION OF THE INVENTION

Figure 1A:
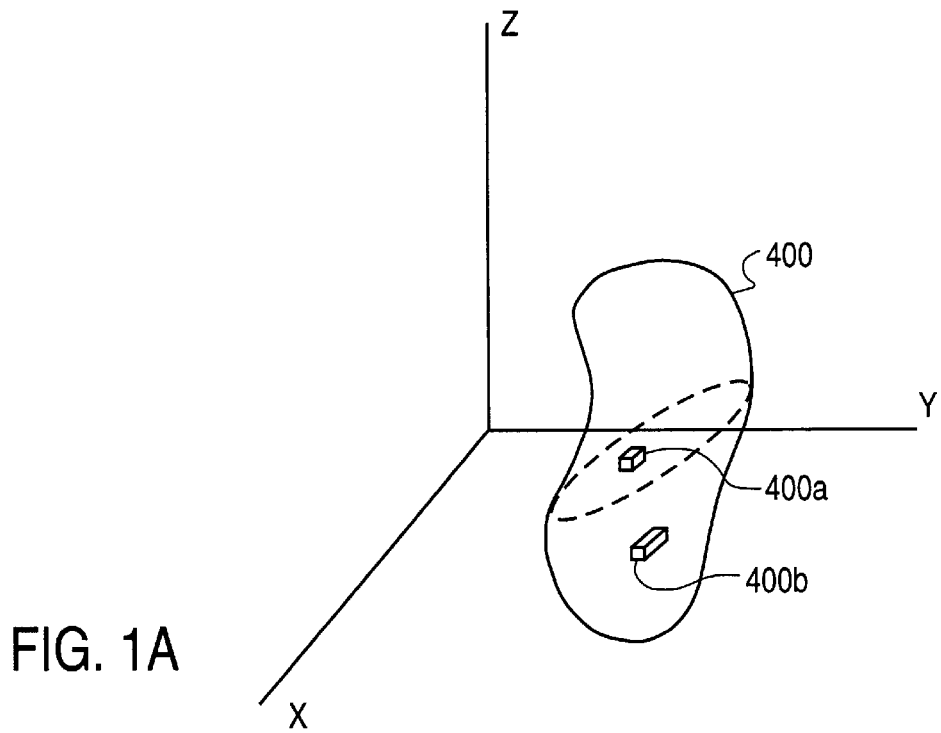
FIG. 1a and FIG. 1b are diagrams of exemplary intensity profiles.

Referring to FIG. 1, a three dimensional illustration of a volume to be treated with radiation is shown. The amount of radiation to be delivered to the volume 400 is not uniform throughout the volume, however. Typically, the amount of radiation to be delivered is highest in the center and decreases outwardly, though not necessarily uniformly. Thus, for example, voxels 400a and 400b could receive different levels of radiation.

Figure 1B:
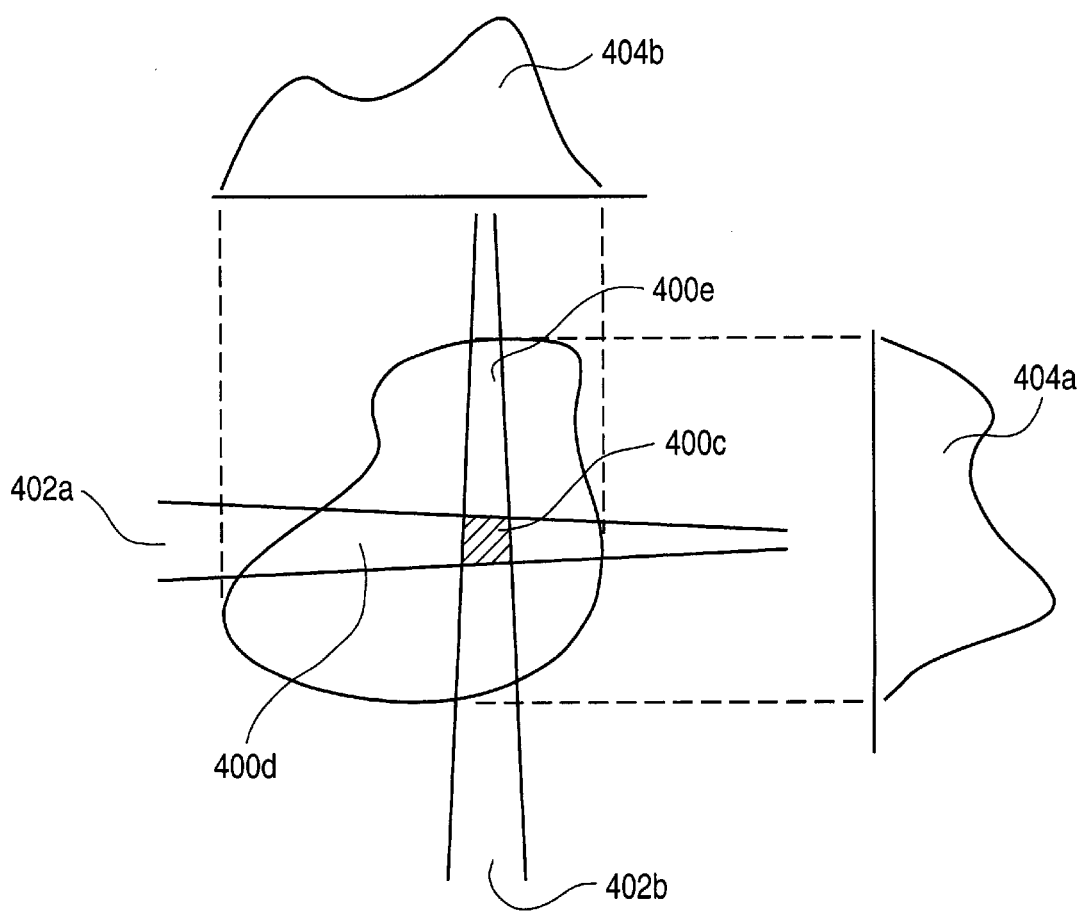

In order to deliver radiation to a specified volume, a plurality of beam settings is typically applied. For example, FIG. 1b illustrates a two-dimensional slice of the volume 400 of FIG. 1a. A pair of intersecting radiation beams 402a, 402b deliver a radiation dose to the volume. The beams 402a and 402b intersect in the cross hatch region 400c, though radiation is delivered along the paths of each of the beams to the volumes 400d and 400e. As can be appreciated, the goal of radiation therapy is to deliver as close a dosage as possible to the prescribed dosage requirements at each of the voxels 400a, 400b etc. The goal of treatment optimization is to determine the best way to achieve this treatment fitting. As shown in FIG. 1b, the radiation beams 402a and 402b coming from intensity profiles 404 and 404b, respectively, at particular gantry angles (an intensity profile is the radiation field over a line of radiation which corresponds to the slice) affect dose volume histograms 404a. Each gantry angle, however, may define a plurality of radiation fields which are to be delivered. Each field is defined as a number of monitor units of dosage to be delivered to a given volume at a particular gantry angle. The leaves of a multi-leaf collimator and/or other shielding device(s) delimit the radiation beam at particular gantry angles and thus define the fields for the particular gantry angle. A graphical user interface in a verification and record system according to the present invention permits easy visualization of each field and intensity maps. In addition, graphics of machine settings and treatment progress are provided for easy visualization control and editing.

Figure 2:
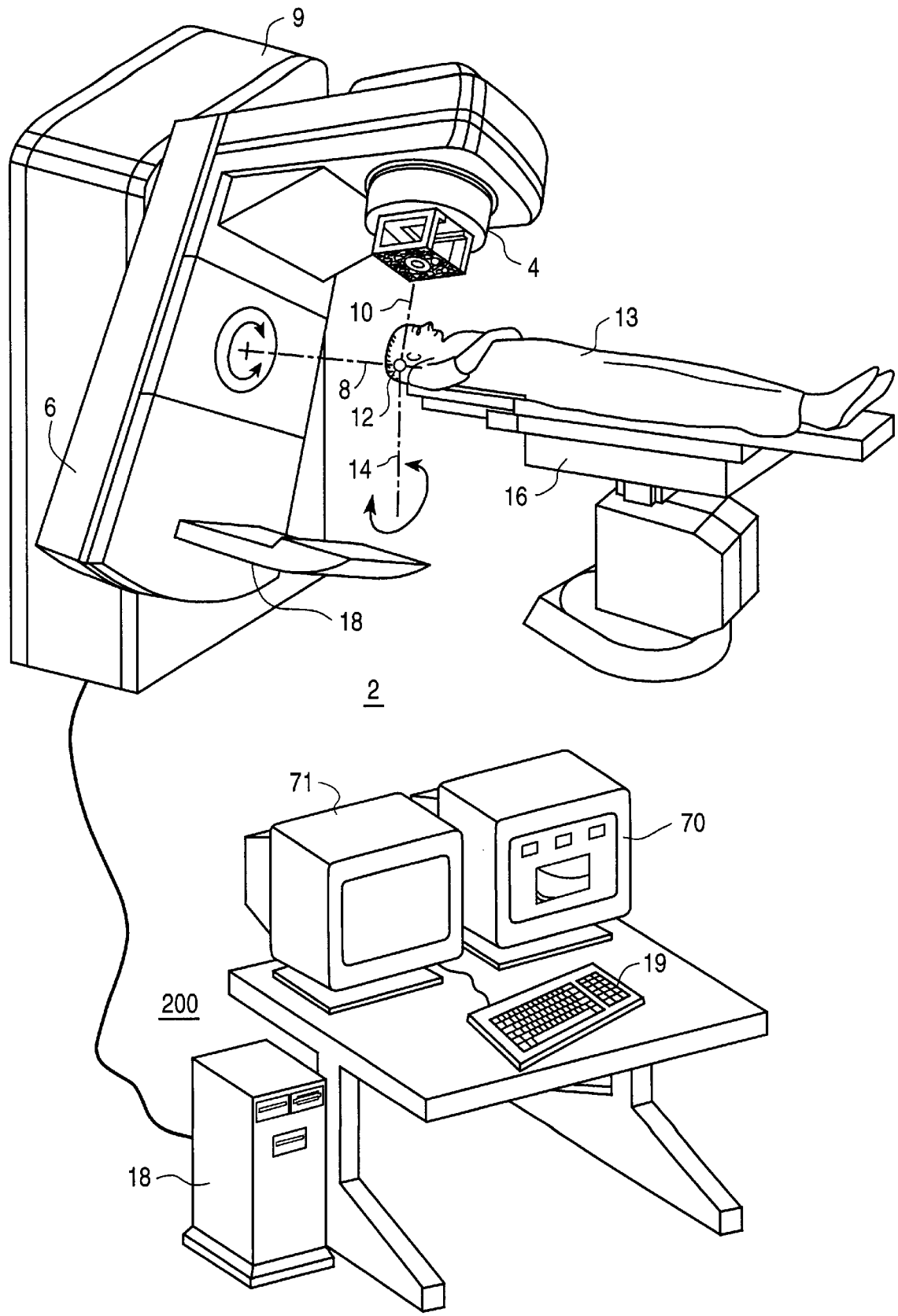
FIG. 2 is a diagram of a radiation treatment device and treatment console according to an embodiment of the present invention.

Turning now to FIG. 2, a radiation treatment apparatus embodying the present invention is shown therein and generally identified by reference numeral 2. The radiation treatment apparatus 2 is representative of, for example, the Mevatron™ series of machines available from Siemens Medical Systems, Inc. The radiation treatment apparatus 2 includes a beam shielding device (not shown) within a treatment head 4, a control unit (not shown) in a housing 9 and a treatment unit 200 according to the present invention. The radiation treatment apparatus 2 includes a gantry 6 which can be swiveled around a horizontal axis of rotation 8 in the course of a therapeutic treatment. The treatment head 4 is fastened to projection of the gantry 6. A linear accelerator is located in the gantry 6 to generate the high powered radiation required for the therapy. The axis of the radiation bundle emitted from the linear accelerator and the gantry 6 is designated by 10. Electron, photon or any other detectable radiation can be used for the therapy.

During the treatment, the radiation beam is trained on a zone 12 of an object 13, for example, a patient who is to be treated and who lies at the isocenter of the gantry rotation. The rotational axis 8 of the gantry 6, the rotational axis 14 of a treatment table 16, and the beam axis 10 intersect in the isocenter.

The area of the patient that is irradiated is known as the field. The plates or leaves of the beam shielding device within the treatment head 4 are substantially impervious to the emitted radiation. The collimator leaves or plates are mounted between the radiation source and the patient in order to delimit the field. Areas of the body, for example, healthy tissue, are therefore subject to as little radiation as possible and preferably to none at all. The plates or leaves are movable such that the distribution of radiation over the field need not be uniform (one region can be given a higher dose than another). Furthermore, the gantry can be rotated so as to allow different beam angles and radiation distributions without having to move the patient.

The radiation treatment device may also include a real-time portal imaging device 11. Such a portal imaging device 11 may be used for treatment verification as is well known. Exemplary portal imaging devices are shown in U.S. Pat. No. 5,138,647, and U.S. patent application Ser. No. 08/808,600, filed Feb. 28, 1997, both assigned to Siemens Medical Systems, Inc., which are hereby incorporated by reference in their entirety as if fully set forth herein.

The radiation treatment device 2 also includes a central treatment processing or control unit 200 which is typically located apart from the radiation treatment device 2. The treatment unit 200 may be a Windows NT workstation, for example. The radiation treatment device 2 is normally located in a different room to protect the therapist from radiation. The treatment unit 200 includes output devices such as at least one visual display unit or monitor 70 and an input device such as a keyboard 19 or other input devices such as a mouse (not shown). Data can be input also through data carriers such as data storage devices or a verification and recording or automatic setup system 102 according to the present invention. By using the keyboard 19 or other input device, the therapist enters into a control unit 76 of the treatment unit 100 the data that defines the radiation to be delivered to the patient. The program can also be input via another input device, for example, using the automatic setup system 102. On the screen of a monitor 76 various data can be displayed before and during the treatment.

The treatment processing unit 200 is typically operated by the therapist who administers actual delivery of radiation treatment as prescribed by an oncologist by using the keyboard 19 or other input device. The therapist enters into the control unit of the treatment unit 200 the data that defines the radiation dose to be delivered to the patient, for example, according to the prescription of the oncologist. The program can also be input via another input device, such as a data storage device. Various data can be displayed before and during the treatment on the screen of the monitor 70.

According to the present invention, the treatment processing unit 200 (and automatic set-up unit 102 (FIG. 3) is further configured to provide graphical representation and control/editing of patient treatment setup information. For example, the monitor 71 may be used for graphical display and editing of machine positions and field shapes. In addition, a pictorial or graphic representation or image of the radiation beams incident upon the target at various gantry angles may be provided. Multiple simple fields may be superimposed on one another in a single graphic so as to easily display an intensity modulation group. Further, a graphic may be provided showing progress of a treatment sequence, by displaying treated fields, untreated fields, and the current treatment field in different colors. Graphic images of the machine settings may be provided for easy reference. The graphic images may be manipulated to adjust machine settings.

Figure 3:
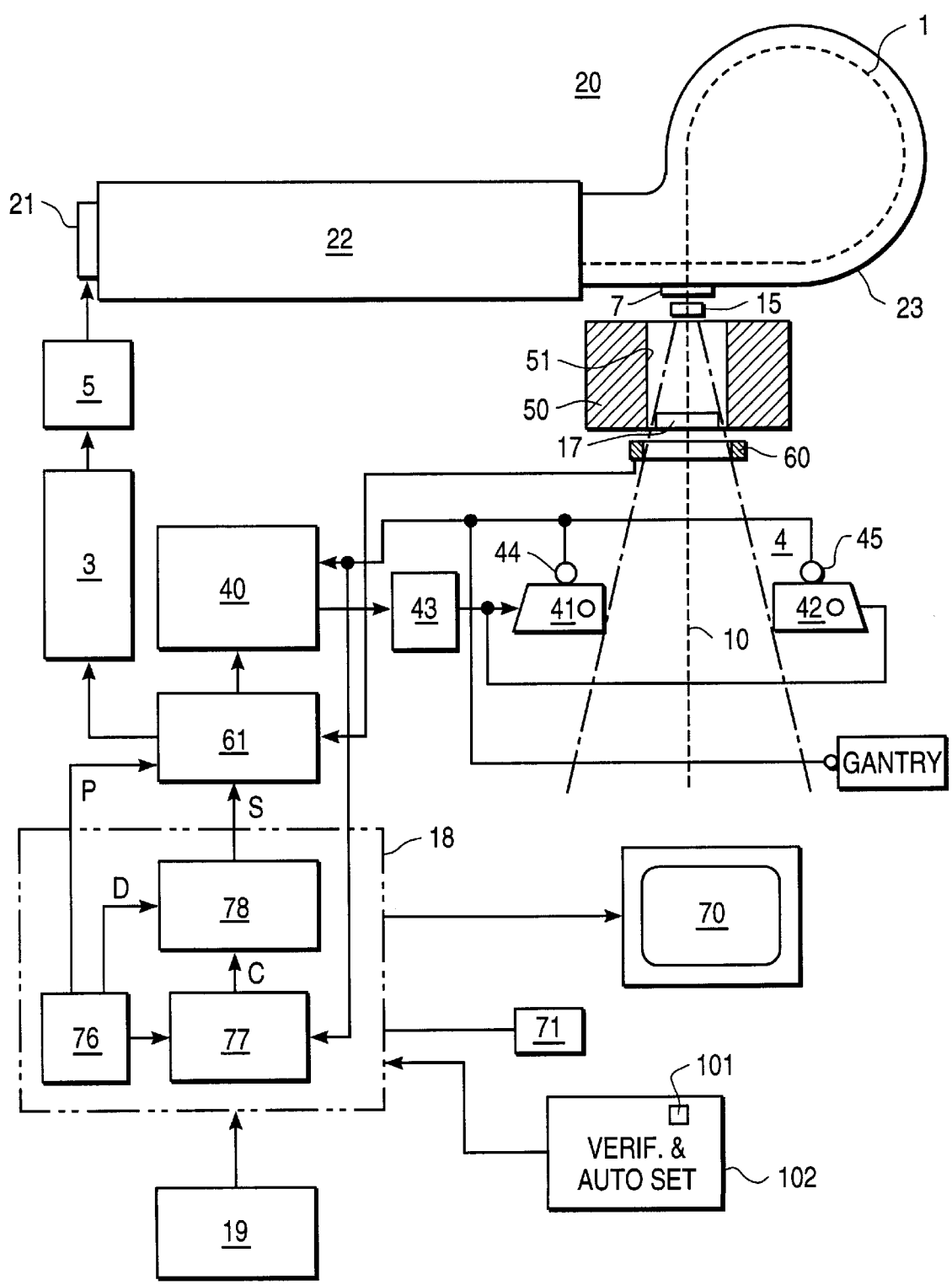
FIG. 3 is a more detailed block diagram illustrating portions of the present invention.

Turning now to FIG. 3, a block diagram of the radiation treatment device 2 and portions of the treatment unit 200 are illustrated in greater detail. An electron beam 1 is generated in an electron accelerator 20. The electron accelerator 20 includes an electron gun 21, a wave guide 22 and an evacuated envelope or guide magnet 23. A trigger system 3 generates injector trigger signals and supplies them to the injector 5. Based on these injector trigger signals, the injector 5 generates injector pulses which are fed to the electron gun 21 in the accelerator 20 for generating electron beam 1. The electron beam 1 is accelerated and guided by the wave guide 22. For this purpose, a high frequency source (not shown) is provided, which supplies radio frequency signals for the generation of an electromagnetic field supplied to the wave guide 22. The electrons injected by the injector 5 and emitted by the electron gun 21 are accelerated by this electromagnetic field in the wave guide 22 and exit at the end opposite to electron gun 21 in electron beam 1. The electron beam 1 then enters a guide magnet 23 and from there is guided through a window 7 along axis 10. After passing through a first scattering foil 15, the beam goes through a passageway 51 of a shield block 50 and encounters a flattening filter 17. Next, it is sent through a measuring chamber 60 in which the dose is ascertained. If the scattering foil is replaced by a target, the radiation beam is an X-ray beam; in this case, the flattening filter 17 may be absent, but it is typically present.

Finally, a beam shielding device is provided in the path of radiation beam 1, by which the irradiated field of the subject of investigation is determined. As illustrated, the beam shielding device includes opposing plates 410 and 420, only two of which are illustrated for convenience. In one embodiment, additional pairs of plates (not shown) may be arranged perpendicular to plates 410 and 420. The plates 410, 420 are moved with respect to axis 10 by a drive unit 43 to change the size of the irradiated field. The drive unit 43 includes an electric motor which is coupled to the plates 410 and 420 and which is controlled by a motor controller 40. Position sensors 44 and 45 are also coupled to the plates 410 and 420, respectively for sensing their positions. An additional beam shielding device may be provided above or below the plates 410, 420. Such a beam shielding device may include, in addition, a multi-leaf collimator having many radiation blocking leaves. Such a multi-leaf collimator, as well as other accessories, such as wedges, are attachable to the treatment head 4. The leaves of such a multi-leaf collimator are illustrated in greater detail in FIG. 4. Opposing leaf, or rod pairs 41a–41n, 42a–42n, each include a motor or drive unit 43a–43n, and 47a–47n, respectively. The drive units drive the rods, or leaves, in and out of the treatment field, thus creating the desired field shape. The rods, or leaves, are typically relatively narrow, and cast a shadow of about 0.5 to 1. cm at isocenter.

Turning back to FIG. 3, the motor controller 40 is coupled to a dose unit 61 which includes a dosimetry controller and which is coupled to a central processing unit 18 for providing set values for the radiation beam for achieving given isodose curves. The output of the radiation beam is measured by a measuring chamber 60. In response to the deviation between the set values and the actual values, the dose control unit 61 supplies signals to a trigger system 3 which changes in a known manner the pulse repetition frequency so that the deviation between the set values and the actual values of the radiation beam output is minimized. In such a radiation device, the dose absorbed by the object 13 is dependent upon movement of the plates and collimator leaves.

The central processing unit 18 is programmed by the therapist according to the instructions of the oncologist and performs optimization so that the radiation treatment device carries out the prescribed radiation treatment. The delivery of the radiation treatment may be input through a keyboard 19 or cursor pointing device (not shown) and graphical user interface according to the present invention. The central processing unit 18 is further coupled to a dose control unit 61 that generates the desired values of radiation for controlling a trigger system 3. The trigger system 3 then adapts the pulse radiation frequency and other parameters in a corresponding, conventional manner. The central processing unit 18 further includes a control unit 76 which controls execution of the program and the opening and closing of the plates and/or leaves 410, 420, 41, 42 and dose signals to deliver radiation according to a desired intensity profile. A memory 77 is also provided for supplying correction signals which the central processing unit 18 may use to adjust the radiation output responsive to position signals received from the position sensors 44, 45. Device settings are viewable through the video monitor 70.

A verification and record or auto set-up system 102 according to the present invention stores and downloads to the radiation system (typically via the CPU 18) the parameters, for example, of the geometry, of the various fields of the course of treatment and wedge correction factors derived during calibration runs for the various fields. Such a verify and record system 102 according to the present invention may be a module of the LANTIS™ (Local Area Network Therapy Information System) available from Siemens Medical Systems, Inc. The automatic set-up or verification and record system 102 may include a processor 101 running a program either independently of, or as a co-processor with, the CPU 18. Both processors may be, for example, x86-type processors, such as Pentium or Pentium II type processors. A graphical user interface according to the present invention may be software running on the system 102. The verification and automatic set-up system 102 may be embodied in a workstation (not shown) remote from treatment unit 200.

Figure 5:
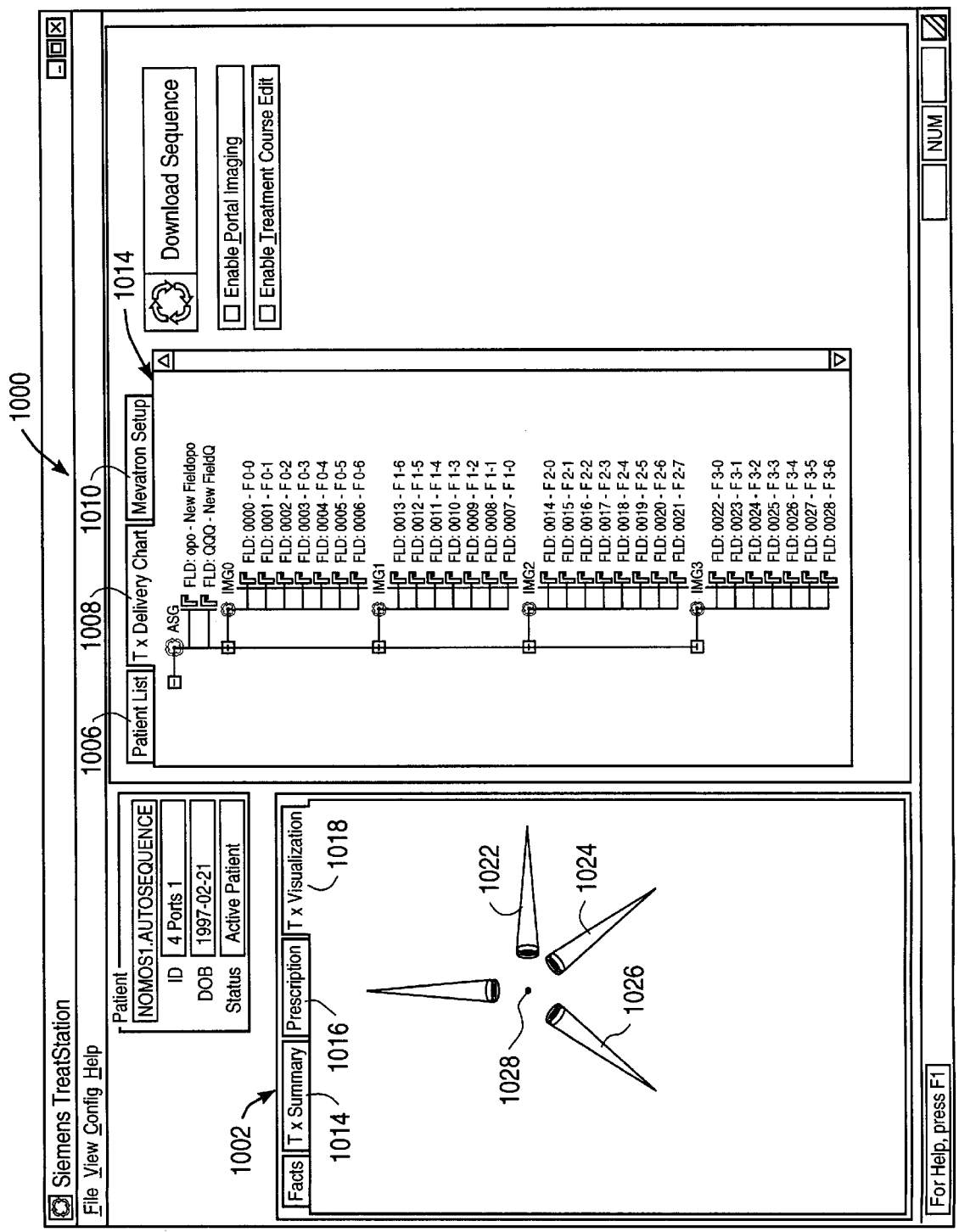
FIG. 5 is a diagram of an exemplary user interfaces according to an embodiment of the invention.

Exemplary graphical user interfaces for use with the verify and record system 102 for controlling operation of the radiation therapy unit 100 are illustrated in FIGS. 5–11. Exemplary software for the user interface according to the present invention is listed in the Appendix. As listed, the code is written in Microsoft Visual C ++, Version 5.0. In addition, certain Microsoft Foundation Classes and O.L.E. controls may be used as building blocks. In particular, an exemplary window 1000 is shown in FIG. 5. The window 1000 includes a visualization window 1002 and a treatment window 1004. The visualization window 1002 as illustrated includes tabs identifying different functionalities. In particular, by clicking on the tabs 1012, 1014, 1016 or 1018, the user may activate a window relating to facts, treatment summary, prescription details and treatment visualization, respectively, as will be described in greater detail below. The image in the visualization window 1002 is directly related to the contents of the treatment window 1004. The treatment window 1004, like the visualization window 1002, includes a plurality of tabs 1006, 1008, 1010, clicking on which permits different functionality. For example, a patient list 1006, a treatment delivery chart 1008, or a linear accelerator setup window 1010 may be activated, as will be described in greater detail below.

As illustrated in FIG. 5, a treatment delivery chart 1008 in hierarchical format is shown. The treatment delivery chart is organized as a folder branch hierarchy, typically according to individual patient. As illustrated, at the top of the hierarchy is an ASG (Automatic Sequencing Group) directory. As will be described in greater detail below, an Automatic Sequencing Group is a distribution of fields which may be delivered automatically by the linear accelerator. In particular, an automatic sequencing group includes unrelated fields whose characteristics are more important than the group. The treatment fields, in turn, may be organized into intensity modulation groups (IMG0–IMG3). The intensity modulation groups are essentially groups of fields which may be delivered sequentially and which have one or more parameters in common, (i.e., the characteristics of the group are more important than the field itself), thereby allowing for common delivery. The radiation therapist may organize the fields by "click and drag" techniques as are well known. Predetermined constraints may prevent the therapist from including a particular field in a particular group. In addition, as will be discussed in greater detail below, the therapist may insert interrupts or portal imaging into the field set-up.

The treatment is delivered in a "top-down" fashion. For example, the treatment delivered in FIG. 5 would be in the following order: FLDOPO, FLDQQQ, IMG0, IMG1, IMG2 and IMG3. The Auto Sequencing Group (ASG), as illustrated in FIG. 5, thus includes a pair of fields FLDOPO, FLDQQQ, and four intensity modulation groups (IMG0–IMG3).

Each field and intensity modulation group shown in the treatment delivery chart 1008 is illustrated as one or more cones 1020 1022, 1024 or 1026 in the treatment summary window 1014. In particular, the tumor or region to be treated is represented by a spot 1028. Each cone 1020, 1022, 1024, 1026 represents the delivery of a radiation field or fields; the radiation being emitted from the apex of the cone and spreading out toward the tumor 1028, as shown similarly in FIG. 1b. As will be described in greater detail below, the graphic is representative of a head-on view of the gantry about its axis of rotation 8 (FIG. 2) (i.e., the axis of gantry rotation is represented as being approximately coincident with the tumor 1028, perpendicular to the screen). It is noted that, in the general case, for the auto sequencing group (ASG) of the treatment delivery chart 1008, when there are two fields and four intensity modulation groups, typically six cones would be visible in the treatment visualization window 1018. However, in the particular case illustrated, the fields FLDOPO and FLDQQQ happen to share the same gantry angle as one of the intensity modulation groups (IMG0–IMG3). Thus, only four cones are visible, the remaining ones being superimposed on others.

Figure 4:
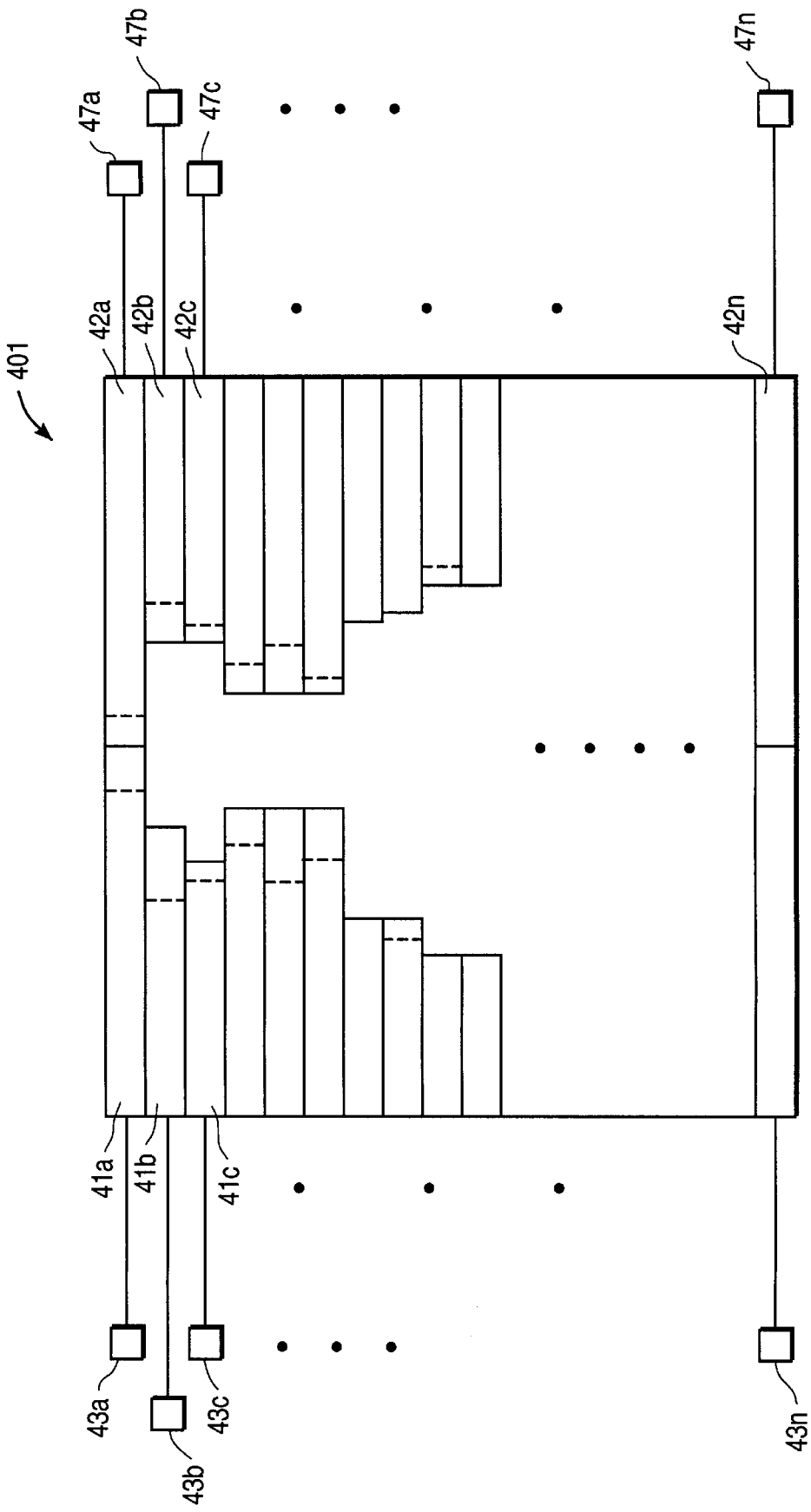
FIG. 4 is a diagram of a multi-leaf collimator according to an embodiment of the invention.
Figure 6A:
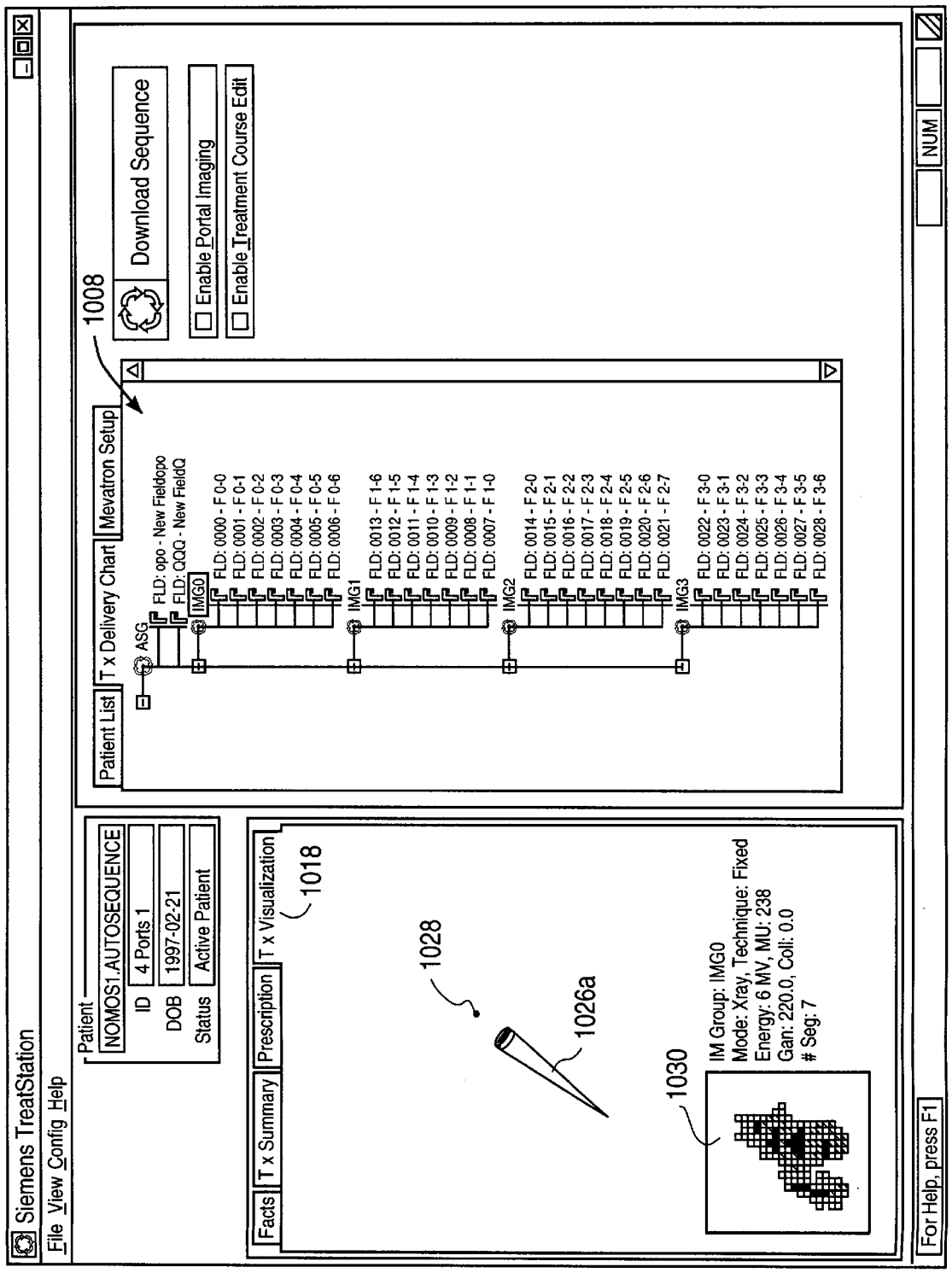
FIGS. 6a and 6b are diagrams of other aspects of the graphical user interface of FIG. 5.
Figure 6B:
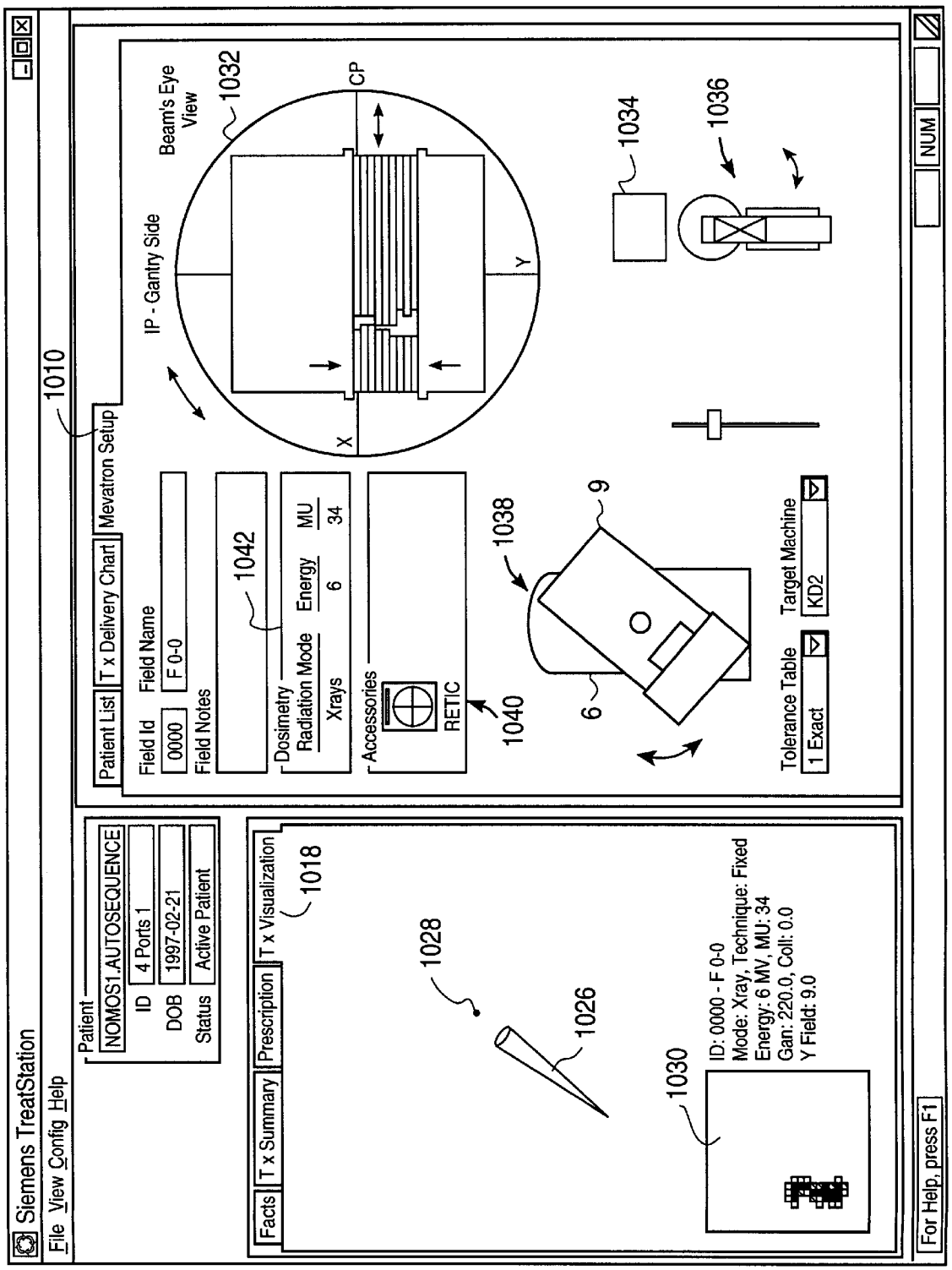

FIGS. 6a–6b illustrate field control and visualization of one field of FIG. 5. In particular, as shown in FIG. 6a, a single field F00 of the intensity modulation group IMG0 has been highlighted. The corresponding linear accelerator setting is visible in the treatment visualization window 1018. In particular, the cone 1026a represents the highlighted field F00 from the setup window 1004. In addition, a visualization icon 1030, representative of collimator settings (FIG. 4, is shown in the treatment visualization window 1018. This is illustrated more clearly in FIG. 6b, in which a setup window 1010 corresponding to the highlighted treatment field of FIG. 6a is shown. The setup window 1010 includes a dosimetry window 1042 which identifies, inter alia, the radiation mode (i.e, X-ray or electron beam), the energy of the field delivery (typically in MV), and the number of monitor units (MU) of radiation to be delivered for the field. In addition, an accessory window 1040 may be provided. The accessory window 1040 identifies, by way of icon, the accessories which may be installed at the treatment head. In particular, these may include, among others, a reticle, a physical wedge or a virtual wedge.

In addition, a graphic image 1032 of a beam's eye view of the beam shielding device jaws 410, 420 and multi-leaf collimator leaves 41i, 42i is shown. As can be seen, the opening in the multi-leaf collimator and jaws corresponds to the shape seen in the icon 1030 of the treatment visualization window 1018.

Also included is a graphic image 1038 of the radiation treatment device 2, including the housing 9 and the gantry 6. The gantry 6 is shown swivelled about its axis of rotation 8, which also corresponds to the angle at which the cone 1026, representative of the emitted radiation, is shown in the treatment visualization window 1018. Finally, the setup window 1010 includes a graphic image 1034 of the treatment table 16. In particular, the table graphic 1034 includes a plan view of the table 1036 and the radiation treatment apparatus structure.

The set-up window 1010 may be used to view and edit the setup of individual treatment fields, as well as program interrupts between field delivery. In particular, the graphic image 1032 of the beam's eye view of the treatment head 2 may be manipulated by a cursor under the control of a mouse or other cursor pointing device, such that the jaws 410, 420 and the leaves 41i, 42i, may be made to open and close, and the treatment head may rotate clockwise or counterclockwise. In addition, the gantry 6 of the graphic 1038 may be made to move about its axis of rotation causing a corresponding movement in the cone 1026. Finally, the graphic 1036 of the treatment table 16 may be made to move about an axis of rotation (corresponding to the center of the circle), as well as move up and down and forward and back. Additionally, different accessories may be chosen using the accessory window 1040. Finally, the radiation mode, energy and number of monitor units applied may be manipulated within the dosimetry window 1042. It is noted that, in practice, oncologist approval must be obtained before the edited treatment may be delivered.

Figure 7:
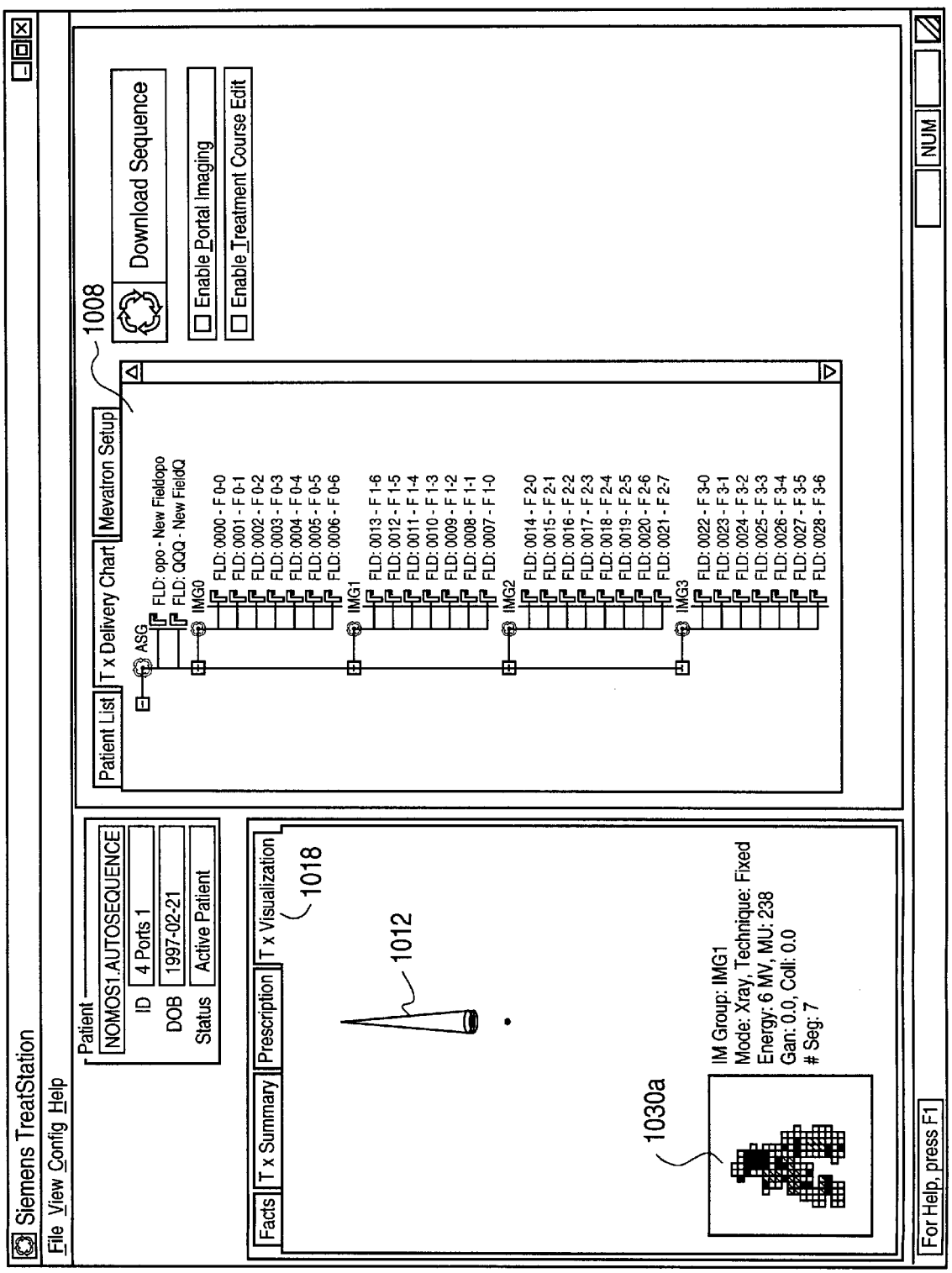
FIG. 7 is a diagram of other aspects of the graphical user interface of FIG. 5.

Turning now to FIG. 7, the treatment visualization window 1018 of an intensity modulated group (in particular, IMG1) is shown. The intensity modulation group (IMG1) is highlighted in the treatment delivery window 1008. A corresponding cone 1020 is shown in the treatment visualization window 1018. It is noted that the treatment cone 1020 of an intensity modulated group (IMG) is distinct from the treatment cone of a single field for easy user reference. In addition to the treatment cone 1020, a visualization icon 1030A is provided, which represents in gray scale form, or color map, a superposition of each of the fields of the intensity modulated group. As discussed above, an intensity modulated group includes a plurality of fields having predetermined common characteristics. The fields, however, may have different intensities at different areas, which are represented for example, in gray scale or color map form in the icon 1030A. In addition, textual information may be provided, such as identification of the intensity modulated group, the mode (i.e., X-ray or electron), the technique (fixed or moving), the energy, and the number of monitor units. In addition, the gantry angle and collimator angle are provided, as well as the number of segments or fields which are superimposed.

Figure 8A:
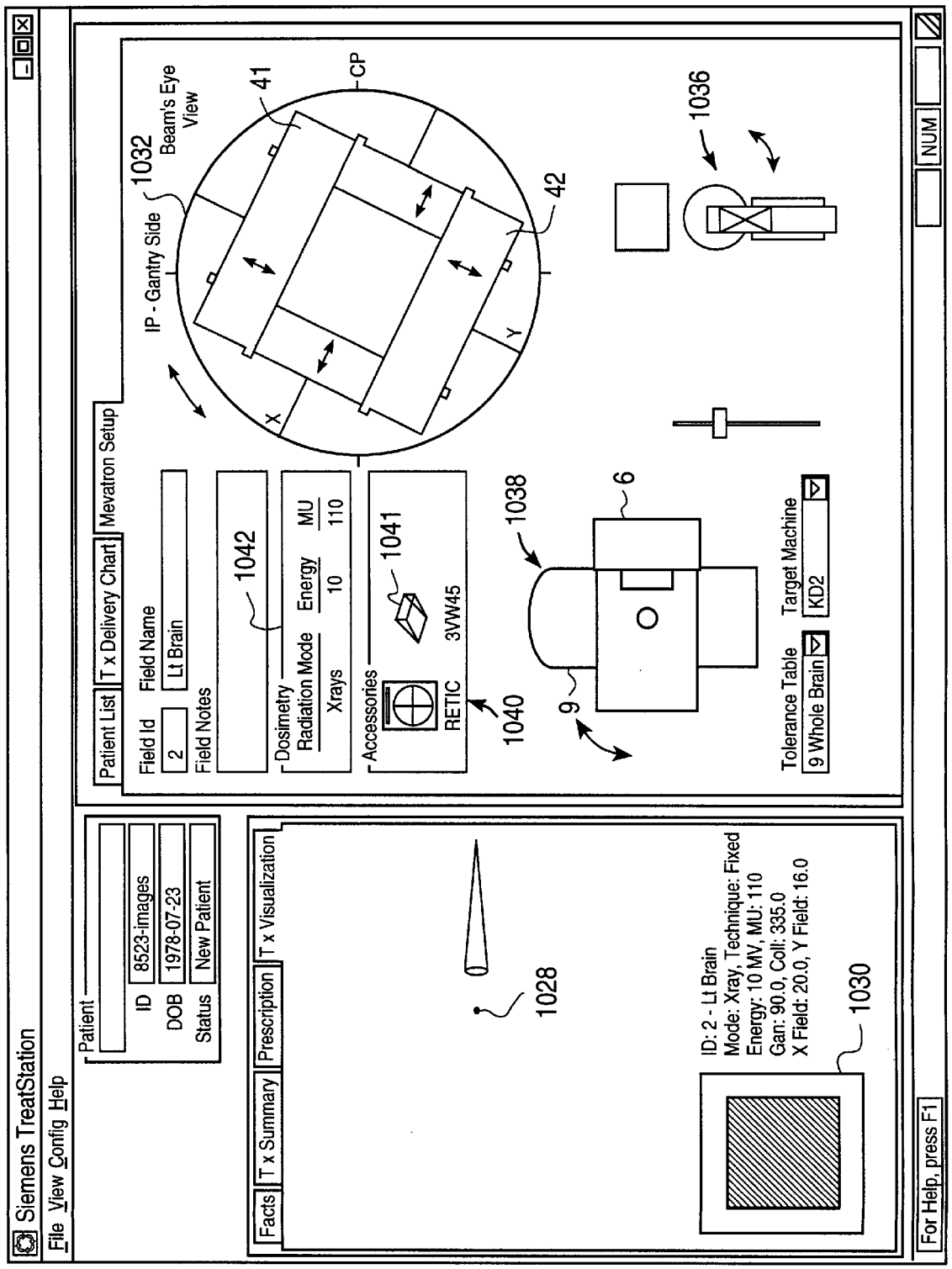
FIGS. 8a and 8b are diagrams of other aspects of the graphical user interface of FIG. 5.
Figure 8B:
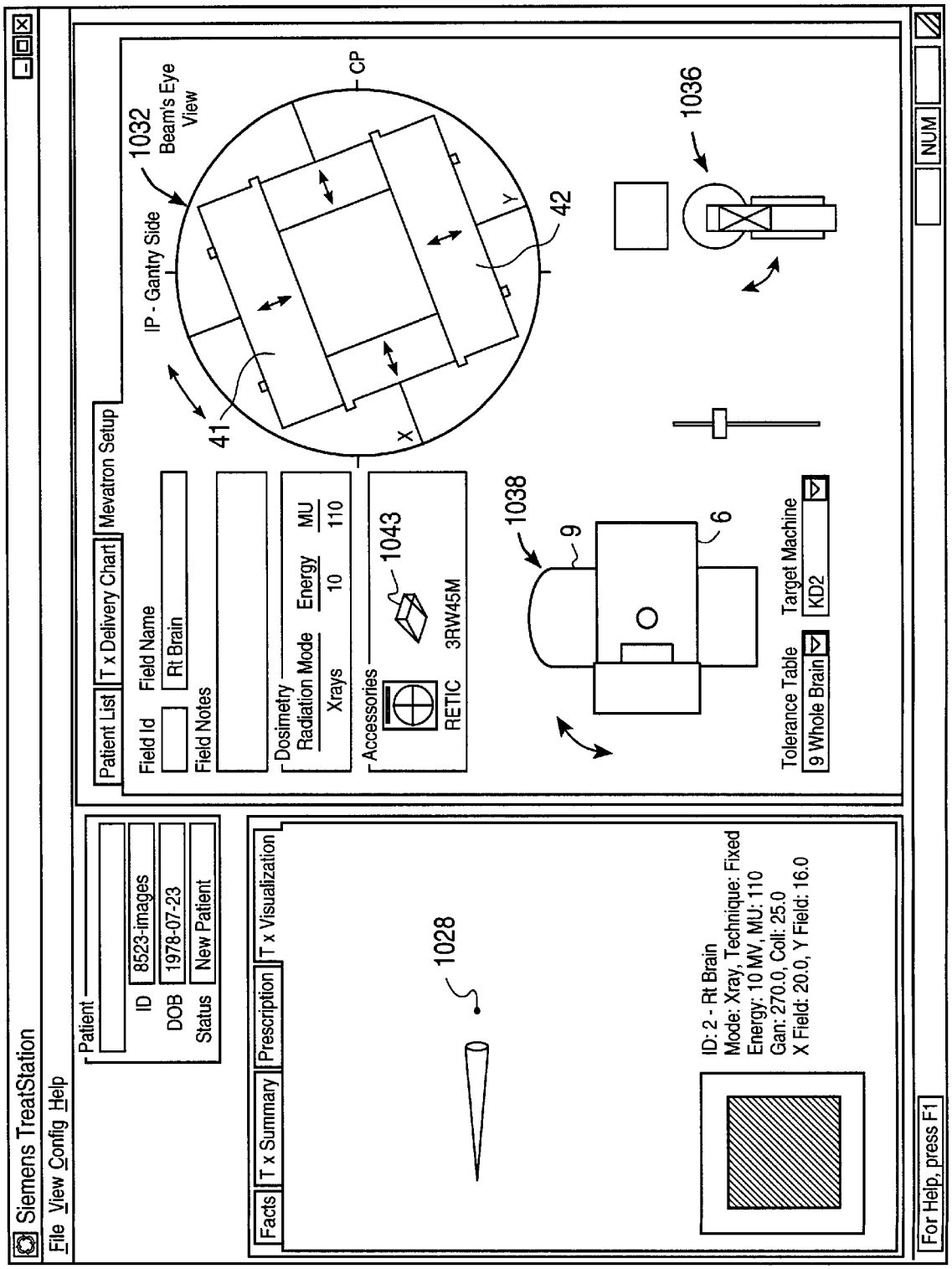

Turning now to FIGS. 8a and 8b, exemplary graphical user interfaces including wedge accessories 1041 (FIG. 8a), 1043 (FIG. 8b) are shown. The graphical user interfaces of FIGS. 8a and 8b are generally similar to FIG. 6b described above. In particular, as illustrated, the setup window displays the beam's eye view 1032 of the treatment of the treatment head 4, the treatment table 1036 and the treatment device 1038, including the gantry 6 disposed at a 90-degree angle from vertical. A corresponding cone is shown in the treatment visualization window. As illustrated, the beam's eye view 1032 includes jaws 410, 420 opened to a predetermined setting. The treatment visualization icon 1030 reflects the setting of the jaws 410, 420. A dosimetry window 1042 and an accessories window 1040 are also provided. A graphical user interface as illustrated in FIG. 8a is used to control a "virtual wedge" accessory. The virtual wedge is illustrated in icon form as icon 1041. Clicking on the icon 1041 may cause establishment of the virtual wedge. As described in U.S. Pat. Nos. 5,563,925, 5,668,847 and U.S. patent application Ser. No. 08/671,914, filed Jun. 28, 1996, all assigned to Siemens Medical Systems, Inc., and hereby incorporated by reference in their entireties as if fully set forth herein, a virtual wedge or compensator accessory enables movement of one or more of the jaws 410, 420 to mimic the presence of a physical wedge. The physical wedge icon is illustrated as icon 1043 in FIG. 8b. The graphical user interface of FIG. 8b is generally similar to that shown in FIG. 8a, except that a colored-in icon 1043 representative of the physical wedge is shown rather than the "clear" icon 1041 representative of the virtual wedge. In addition, as illustrated in FIG. 8b, the gantry 6 is set to a 270° angle from vertical. It is noted that in both FIG. 8a and FIG. 8b, the treatment head 4 has been rotated at a rotation angle reflected in the visualization icons 1030. It is further noted that functionality may be provided whereby moving a cursor over a graphic (either the particular machine graphic or cone or visualization icon) causes a display, in textual format, of machine settings.

Figure 9:
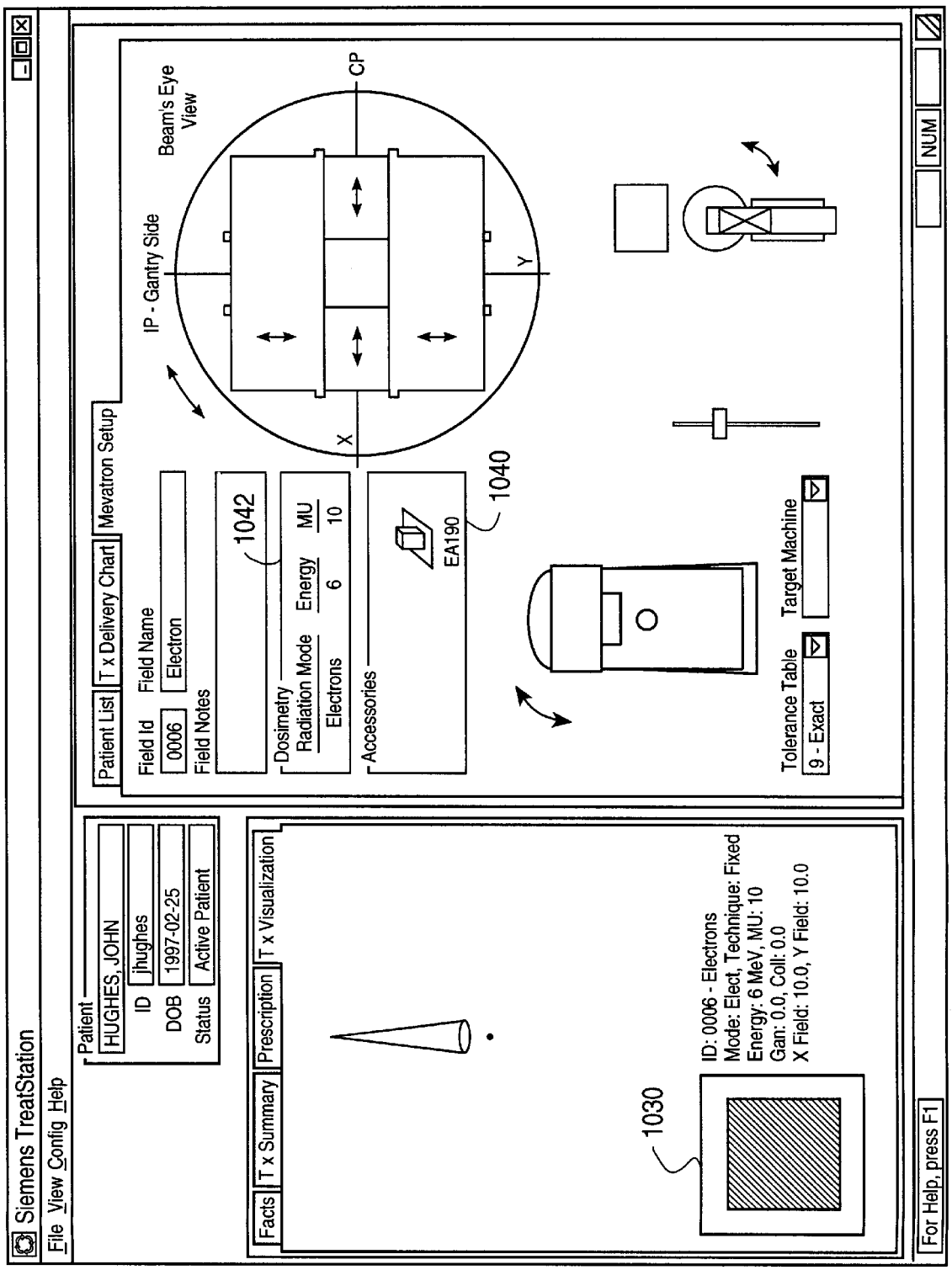
FIG. 9 is a diagram of other aspects of the graphical user interface of FIG. 5.

As discussed above, the radiation therapy device 2 according to the present invention can also be used in an electron mode. Thus, as illustrated in FIG. 9, the dosimetry window 1042 indicates that the radiation mode is "electrons." In addition, the accessories window 1040 displays accessories for electron treatment delivery. Finally, the visualization icon 1030 provides for a visualization of the setting of the jaws 41, 42 and indicates that the mode is electron mode and the energy is in electron volts.

Figure 10:
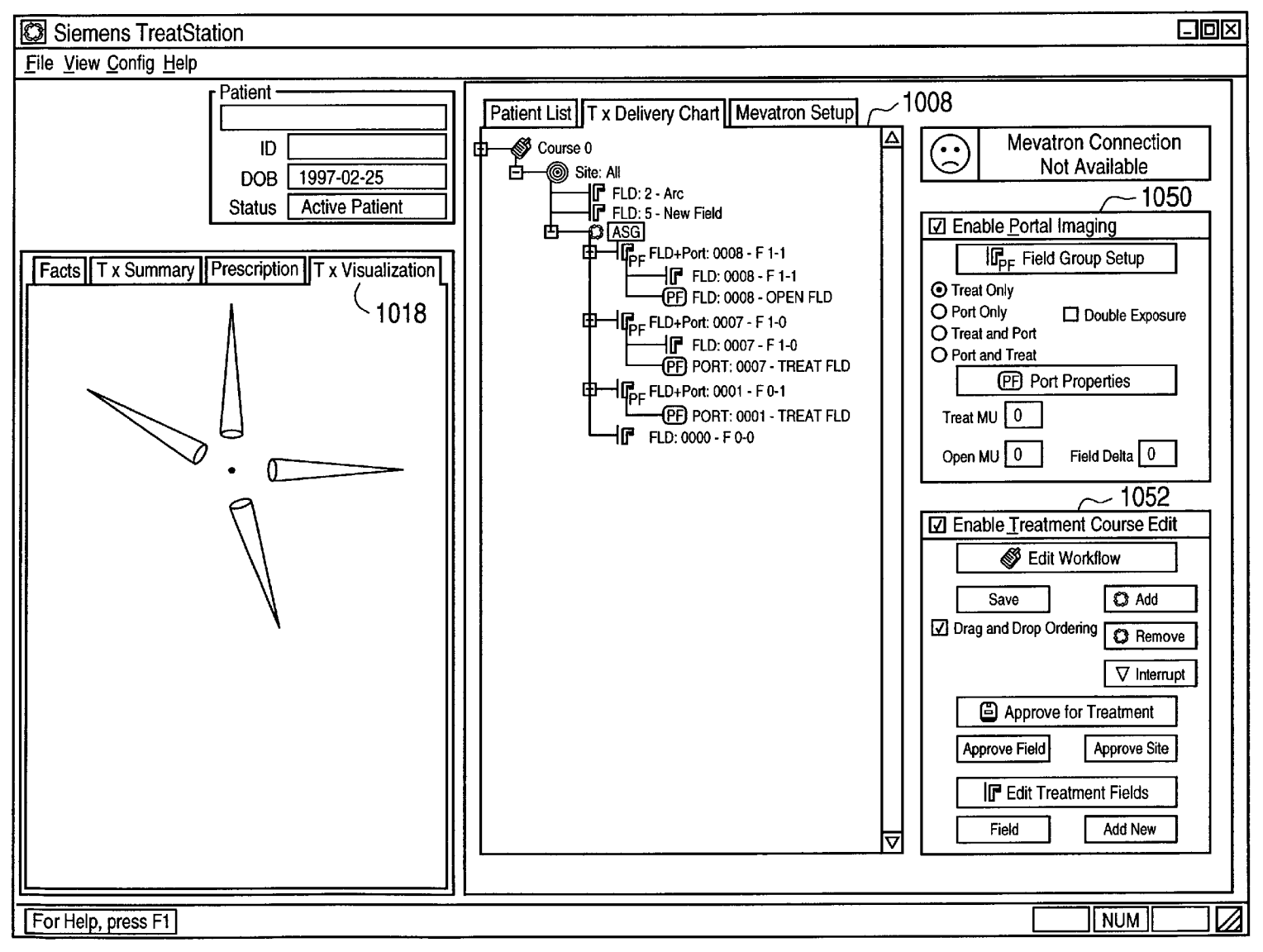

Turning now to FIG. 10, another variation of the graphical user interface is illustrated. In particular, the treatment delivery chart shown in FIG. 10 includes a treatment window 1052 and portal imaging window 1050. As discussed above, the graphical user interface according to the present invention permits editing of treatment fields and ordering of field delivery. In addition, fields may be added, removed and interrupted by use of the appropriate functions available from the treatment editing window 1052.

As illustrated in FIG. 10, a graphical user interface according to the present invention further includes the ability to control portal imaging, by way of the portal imaging window 1050. As is well known, portal imaging employs the radiation emitted from the radiation therapy device (at a low level) in order to take, for example, X-ray images of the area to be treated. The portal images are taken at the same machine settings, including collimator settings and gantry angles as the actual treatment fields. Accordingly, the treatment delivery chart 1008 of FIG. 10 illustrates four fields in the automatic sequencing group ASG. In particular, fields F00, F01, F10 and F11 are illustrated. Fields F01, F10 and F11 also include portal imaging. In particular, portal imaging fields Port 0001, Port 0007 and Port 0008 are to be delivered. The tree hierarchy of the treatment delivery chart 1008 illustrates this by way of PF folders associated with the corresponding fields FLD. The portal imaging may be edited, for example, by clicking on the appropriate folder and the portal imaging window 1050.

Figure 11:
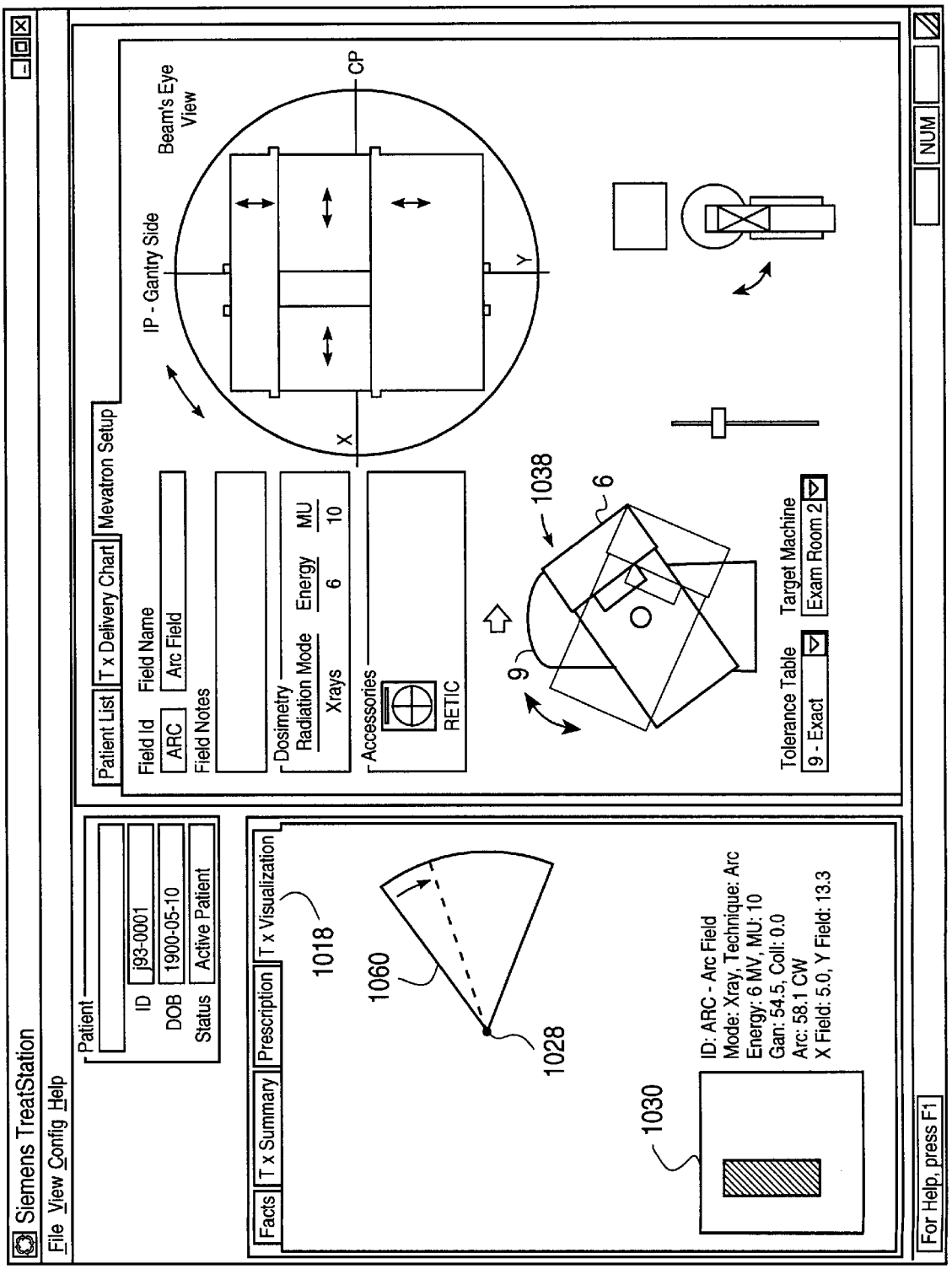
FIG. 11 is a diagram of other aspects of the graphical user interface of FIG. 5.

It is noted that a field FLD2 outside of the automatic sequencing group ASG of FIG. 10 is provided. The FLD2 defines an arc treatment field. An arc treatment field involves, inter alia, a treatment delivered by continuous rotation of the gantry 6 while radiation is being applied. Control of an arc treatment field is illustrated in FIG. 11. In particular, the treatment visualization window 1018 includes an arc 1060 representative of the angle through which the gantry is to move. The treatment visualization icon 1030 shows the settings of the beam shielding device and identifies that the treatment is an arc treatment and the angle over which the gantry is to move. The gantry icon 1038 shows beginning and ending positions of the gantry 6, as well as the direction of rotation of the gantry. During the course of treatment, the arc 1060 may fill in in a different color representative of delivered radiation.

Figure 12:
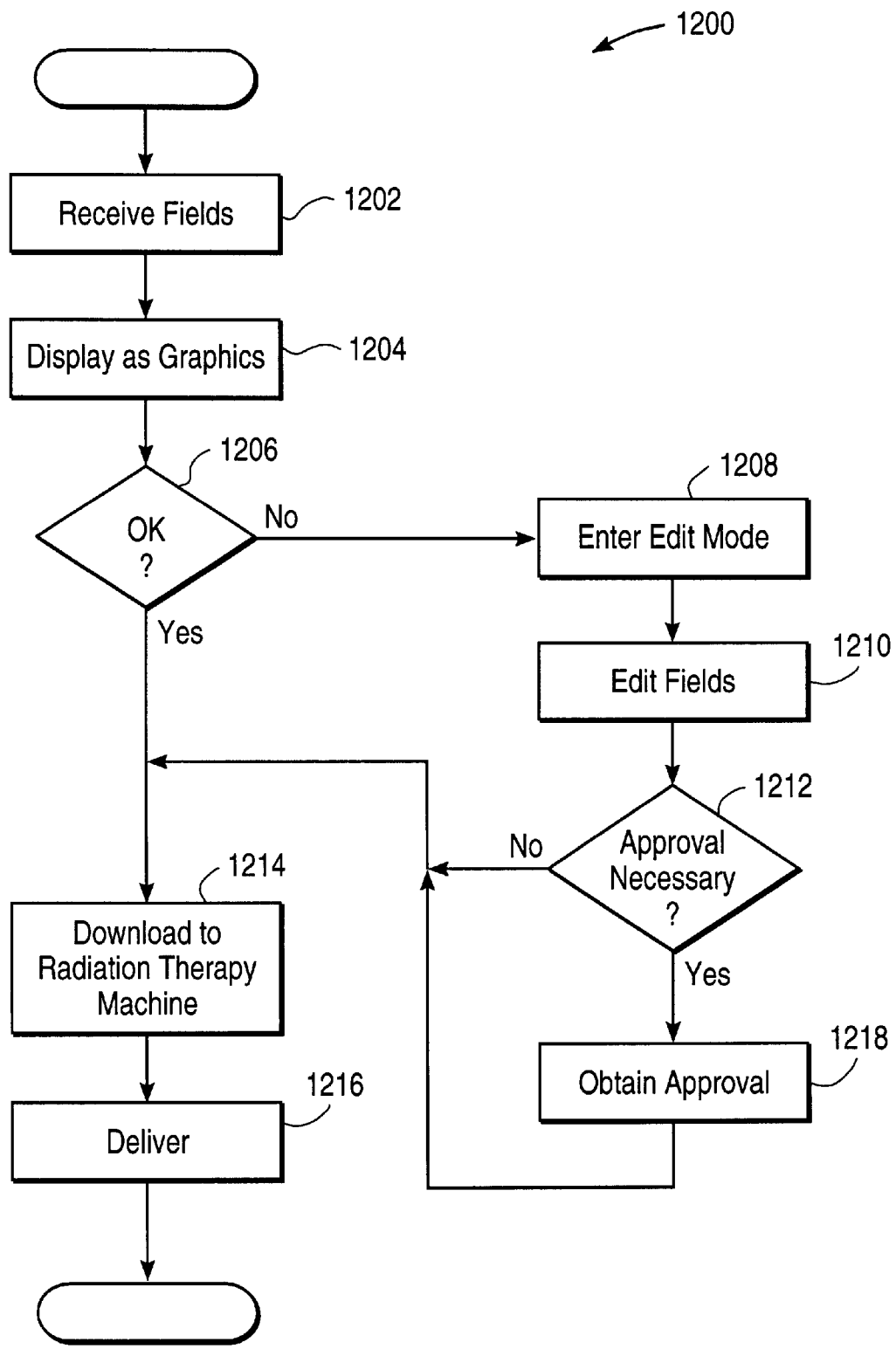
FIG. 12 is a flowchart illustrating operation of an embodiment of the present invention.

Turning now to FIG. 12, a flowchart 1200 illustrating operation of a method according to an embodiment of the present invention is shown. In a step 1202, the verification and record/automatic setup system 102 receives treatment fields. As discussed above, the treatment fields may be received by an optimization engine using prescription parameters or may be directly input via keyboard. In a step 1204, a processor associated with the verification and record system 102, such as CPU 101, generates a graphical user interface according to the present invention from the set of the received fields. As discussed above, the fields may be organized into a tree or folder hierarchy and may be organized into intensity modulated groups or automatic sequencing groups. If, in a step 1206, the organization of the treatment fields is approved, then in a step 1214, the set of fields is downloaded to the radiation therapy machine 2. In a step 1216, the radiation therapy is delivered according to the set of fields. If, however, in step 1206, modification of the organization of the set of fields received in step 1202 or editing of the fields themselves is desired, then in a step 1208, the graphical user interface, according to the present invention, may permit entering an edit mode. In a step 1210, the system may allow editing the fields. As discussed above, editing the fields may include reorganizing auto-sequencing groups and intensity modulation groups, inserting interrupts, and portal imaging. In addition, editing may include editing the individual treatment fields themselves, such as by adjusting the treatment head 4 and beam shielding devices, selecting or changing accessories, changing gantry or table settings, adjusting energy settings, and the like. Once the treatment fields have been edited, the system determines whether or not approval, for example, by an oncologist, is necessary in a step 1212. Such approval may be necessary if actual field settings are edited (as opposed to merely changing the organization of already predetermined fields). If such approval is not necessary, then the treatment will be downloaded to the radiation therapy machine in a step 1214 and the treatment will be delivered in step 1216. If, however, approval is necessary then approval must be obtained in a step 1218 and keyed in, for example, by a password prior to downloading and delivering the radiation therapy.

Figure 13:
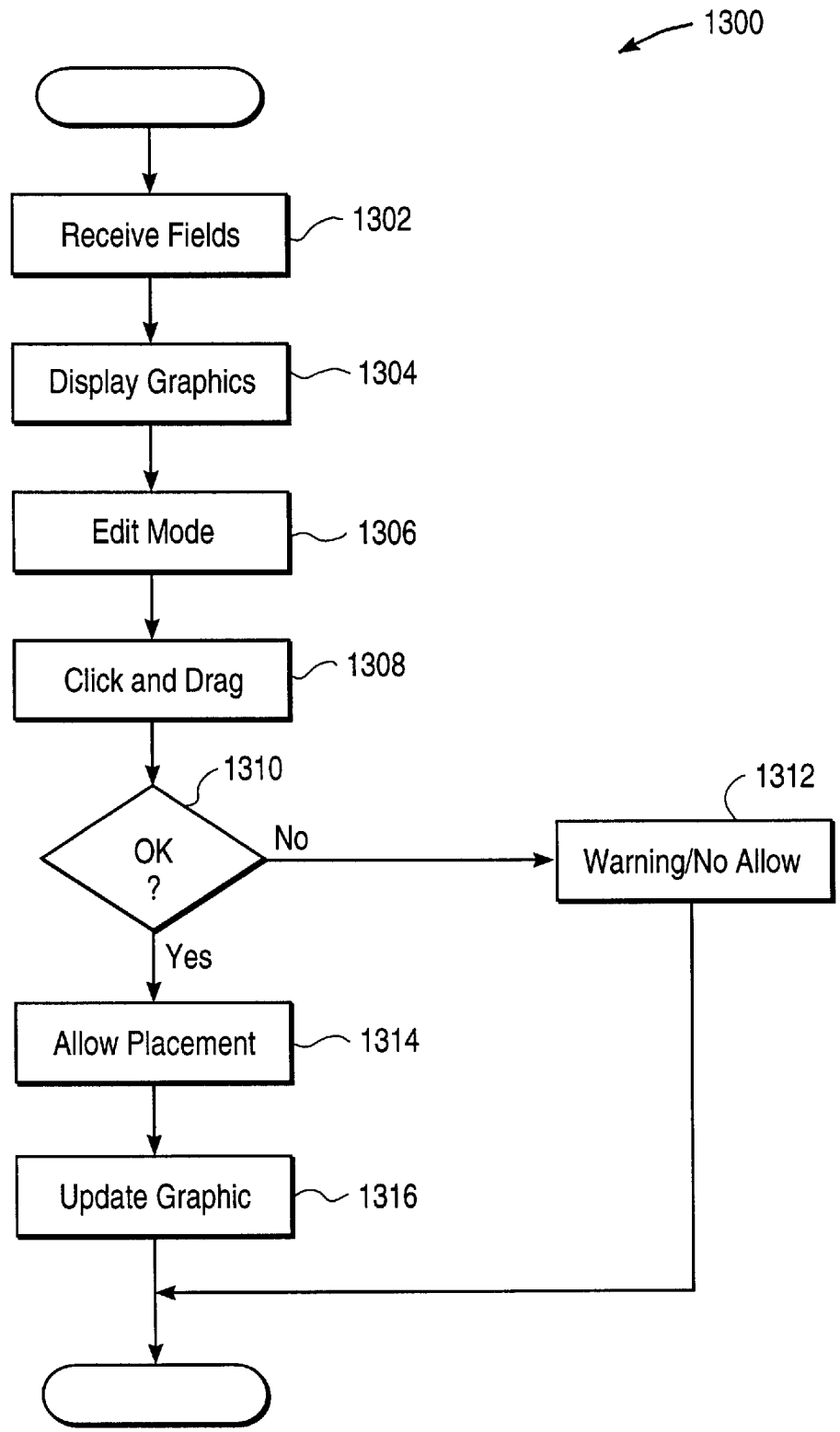
FIG. 13 is a flowchart illustrating operation of an embodiment of the present invention.

Turning now to FIG. 13, a flowchart illustrating operation of a method for re-organizing treatment fields according to an embodiment of the present invention is illustrated. In particular, in a step 1302, a plurality of radiation fields are delivered, as discussed above. In a step 1304, the radiation fields are displayed, for example, in a tree hierarchy in the delivery chart 1008. In a step 1306, an edit mode may be entered. In a step 1308, the sequencing of the fields may be changed by clicking and dragging a particular field from one location to another. In a step 1310, the system will determine whether or not a predetermined relocation of a field is allowed. For example, in FIG. 5, the system will determine whether movement of field FLD0007 is permitted to the space between field 0014 and field 0015. If the movement is not allowed, then in a step 1312, the graphical user interface will display a warning and will not allow the transposition of the field. If, however, the movement of the field is permitted, then the placement of the field will be allowed in a step 1314. Finally, in a step 1316, the graphics, such as the graphics in the treatment visualization window 1018 and/or the setup window 1010, may be updated accordingly to the new organization.

Figure 14:
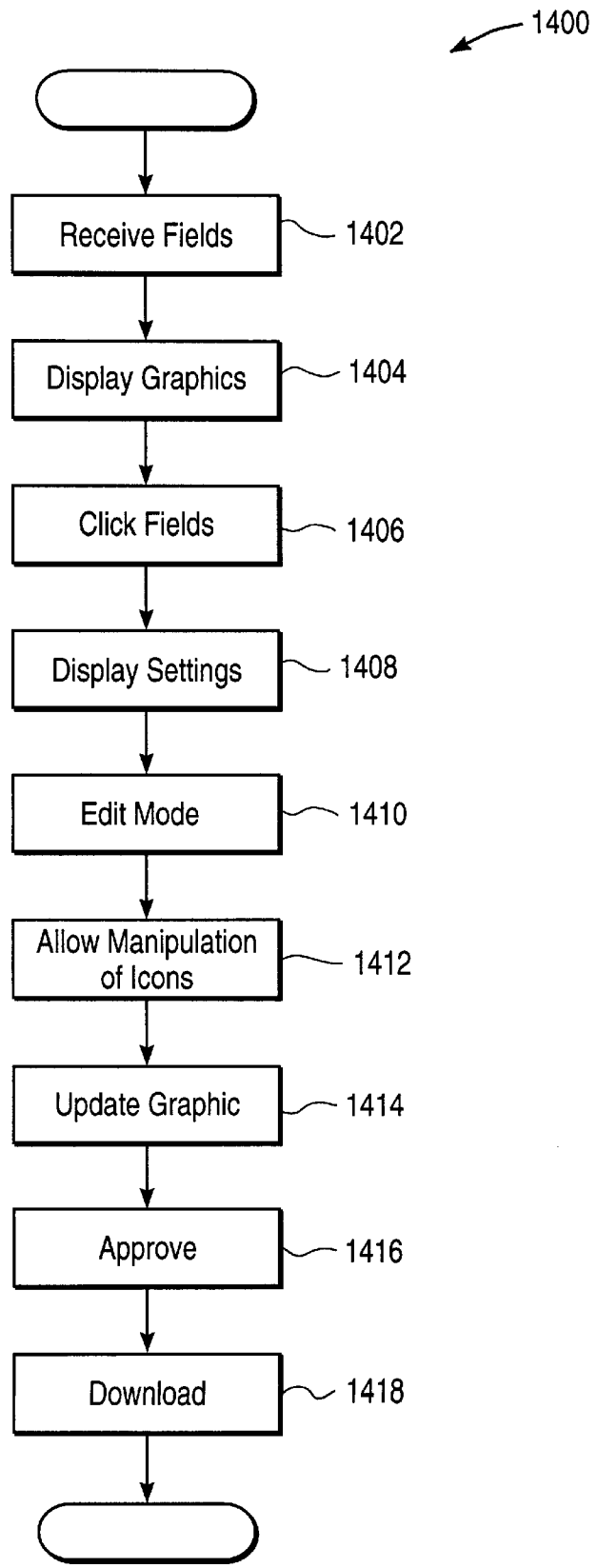
FIG. 14 is a flowchart illustrating operation of an embodiment of the present invention.

Turning now to FIG. 14, a flowchart illustrating a method 1400 for controlling a radiation therapy machine 2 using a graphical user interface according to another embodiment of the present invention is illustrated. In particular, in a step 1402, a plurality of treatment fields are downloaded to the automatic setup device 102. In a step 1404, the received fields are organized into a display, such as in the delivery chart 1008 of the treatment window 1014. In a step 1406, the system permits the user to click on individual fields. Once the individual fields have been clicked on, for example, by a cursor pointing device, then in a step 1408, the system will display the machine settings, for example, in setup window 1010. The system may enter a setup mode or edit mode in a step 1410, for example, by clicking on an enable treatment edit window 1052 (FIG. 10). In the edit mode, in a step 1412, manipulation of machine icons is permitted. For example, the beam's eye view 1032 of the treatment head 4 may be manipulated in a clockwise or counterclockwise direction, the jaws 410, 420 may be opened or closed, or individual leaves of the multi-leaf collimator may be opened or closed. Similarly, the graphic image icon 1038 of the linear accelerator may be manipulated such that the gantry 6 may be rotated in a clockwise or counterclockwise fashion. In addition, the table icon 1036 may be manipulated such that the table may be rotated or adjusted in a different fashion. Similarly, accessories may be selected from the accessory window 1040 and dosimetry may be altered via use of the dosimetry window 1042. Once the settings have been changed, in a step 1414, other visualization graphics may be updated. For example, the cones in the treatment visualization window 1018 may be reset to different angles and the settings in the visualization icons 1030, 1030A may similarly be updated, as may the textual information provided therewith. In a step 1014, approval of the edits may be obtained, for example, by clicking on an approval icon in the treatment edit window 1052 (FIG. 10). Once approval has been obtained, the treatment may be downloaded in a step 1418 to the radiation therapy device.

Figure 15:
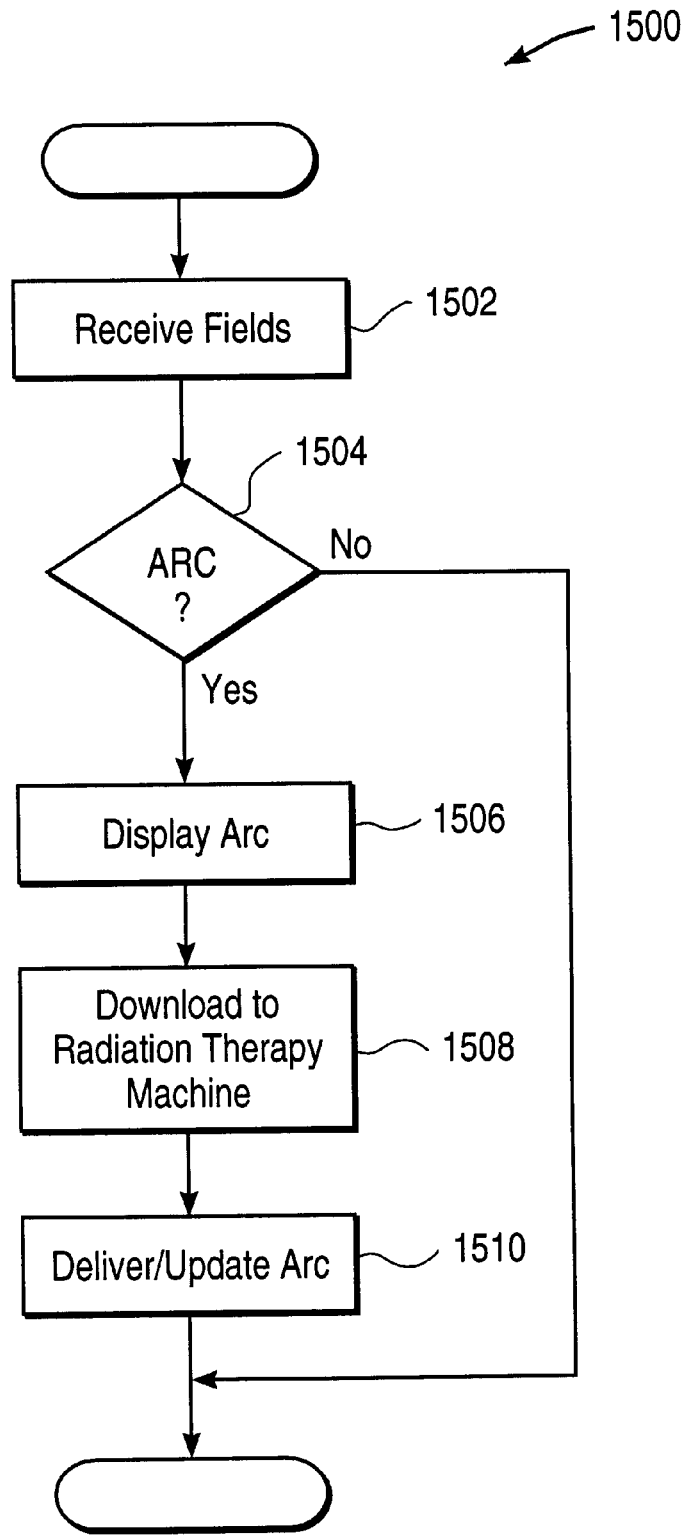
FIG. 15 is a flowchart illustrating operation of an embodiment of the present invention.

Turning now to FIG. 15, a flowchart 1500 showing operation of a method 1500 for controlling arc therapy according to an embodiment of the present invention is illustrated. In particular, in a step 1502, the system receives fields in a manner similar to that described above. In a step 1504, the system determines whether any of the fields are arc therapy fields. If not, then the system continues as described above. However, if in step 1504, certain fields were identified as arc fields, then the arc fields may be displayed as arcs (distinguished from the cones representative of the other fields). The arcs indicate initial and final positions of the gantry 6. In addition, the icon 1038 representative of the gantry will show initial and final positions of the gantry 6. In a step 1508, the arc field may be downloaded to the radiation therapy device. The radiation therapy device will then perform the arc treatment and will provide status updates to the automatic setup system 102 and control unit 200. As such, the arc treatment display icon 1060 (FIG. 11) will show areas of the arc treatment that have been treated or not treated.

The invention described in the above detailed description is not intended to be limited to the specific form set forth herein, but is intended to cover such alternatives, modifications, and equivalents as can reasonably be included within the spirit and scope of the appended claims. For example, in alternate embodiments, the unit 102 may directly control the radiation therapy device, without need for separate downloading.

What is claimed is:

1. A graphical user interface for a radiation therapy device, comprising:

gantry;

means for generating graphic images representative of at least predetermined portions of structure of said gantry; and means for controlling said gantry by manipulating said graphic images representative of said at least predetermined portions of structure of said gantry.

2. A graphical user interface according to claim 1, including means for displaying status updates of a course of treatment.

3. A graphical user interface according to claim 1, said controlling means including means for setting a gantry angle by manipulating a graphic image of said gantry.

4. A graphical user interface according to claim 1, said controlling means including means for setting a beam shielding device by manipulating an image of said beam shielding device.

5. A graphical user interface according to claim 1, further including means for displaying radiation intensities corresponding to deliverable radiation fields.

6. A graphical user interface as recited in claim 5, wherein said displaying means includes means for displaying intensity levels for a plurality of fields super-imposed on one another.

7. A graphical user interface as recited in claim 1, further including means for generating images representative of one or more radiation beams.

8. A graphical user interface according to claim 1, further including means for displaying textual information associated with said graphic images.

9. A graphical user interface according to claim 7, wherein said generating means generates images corresponding to arc treatments.

10. A graphical user interface according to claim 7, wherein said generating means generates images corresponding to individual fields.

11. A graphical user interface according to claim 7, wherein said generating means generates images corresponding to a plurality of fields representative of intensity modulated groups.

12. A method for controlling a radiation treatment apparatus, comprising:

generating graphic images representative of at least predetermined portions of structure of said radiation treatment apparatus; and manipulating said graphic images representative of said at least predetermined portions of structure of said radiation treatment apparatus to control settings of said radiation treatment apparatus.

13. A method according to claim 12, including displaying graphic status updates of a course of treatment.

14. A method according to claim 12, said manipulating including by manipulating a graphic image of a gantry to set a gantry angle.

15. A method according to claim 12, said manipulating including manipulating an image of a beam shielding device to set said beam shielding device.

16. A method according to claim 12, further including displaying radiation intensities corresponding to deliverable radiation fields.

17. A method according to claim 16, wherein said displaying includes displaying intensity levels for a plurality of fields super-imposed on one another.

18. A method according to claim 12, further including generating images representative of one or more radiation beams.

19. A method according to claim 12, further including displaying textual information associated with said graphic images.

20. A method according to claim 18, wherein said generating includes generating images corresponding to arc treatments.

21. A method according to claim 18, wherein said generating includes generating one or more images corresponding to individual fields.

22. A method according to claim 18, wherein said generating includes generating one or more images corresponding to a plurality of fields representative of intensity modulated groups.

23. A radiation therapy device, comprising:

a gantry; and a controller configured to control an orientation of said gantry, said controller including a graphical user interface, wherein said graphical user interface displays images representative of one or more orientations of structure of said gantry, said orientations controllable by manipulation of said images.

24. A radiation therapy device in accordance with claim 23, said images comprising images of radiation beams being emitted from a radiation head associated with said gantry.

25. A radiation therapy device in accordance with claim 23, said images comprising images representative of orientations of one or more radiation blocking devices associated with said gantry.

26. A radiation therapy device in accordance with claim 23, said images comprising images representative of a radiation arc being delivered through a movement of said gantry.

* * * * *